(12) United States Patent
Sieverding et al.

(10) Patent No.: US 6,696,497 B2
(45) Date of Patent: Feb. 24, 2004

(54) FUNGICIDAL MIXTURES

(75) Inventors: Ewald Sieverding, St. Johann (DE); Gunter Reichert, Bubenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/782,095

(22) Filed: Feb. 13, 2001

(65) Prior Publication Data

US 2002/0065313 A1 May 30, 2002

Related U.S. Application Data

(60) Provisional application No. 60/184,277, filed on Feb. 23, 2000.

(51) Int. Cl.$^7$ .......................... A01N 35/02; A01N 47/12
(52) U.S. Cl. ..................... 514/687; 514/479; 514/484; 514/487
(58) Field of Search ................ 514/687, 479, 514/484, 487

(56) References Cited

U.S. PATENT DOCUMENTS

| 5,453,531 A | 9/1995 | Seitz et al. ............... 560/29 |
| 5,773,663 A | 6/1998 | Curtze et al. ............. 568/333 |
| 5,776,976 A | 7/1998 | Dehne et al. ............. 514/479 |
| 5,814,669 A | 9/1998 | Stelzer et al. ............ 514/626 |
| 5,847,194 A | 12/1998 | Wetterich et al. .......... 560/28 |
| 5,962,518 A | 10/1999 | Stenzel et al. ............ 514/491 |
| 2003/0068303 A1 * | 4/2003 | Selvig et al. ............. 424/93.1 |
| 2003/0118614 A1 * | 6/2003 | Sieverding et al. ......... 424/400 |

FOREIGN PATENT DOCUMENTS

| DE | 4321897 | 1/1995 |
| DE | 19531814 | 3/1997 |
| EP | 1023834 | 8/2000 |
| IE | 912997 | 12/1992 |
| JP | 09323984 | 12/1997 |
| WO | 99/56551 | 11/1999 |
| WO | 00/72677 | 12/2000 |
| WO | 00/72678 | 12/2000 |
| WO | WO 00/76317 | 12/2000 |

OTHER PUBLICATIONS

S.R. Colby, "Calculating Synergistic and Antagonistic Responses to Herbicide Combinations", Weeds, 15, 1967, pp. 20–22.

* cited by examiner

Primary Examiner—John Pak
(74) Attorney, Agent, or Firm—Keil & Weinkauf

(57) ABSTRACT

A fungicidal composition comprises an acceptable carrier and/or surface active agent and a synergistically effective amount of (a) at least one benzophenone of formula I

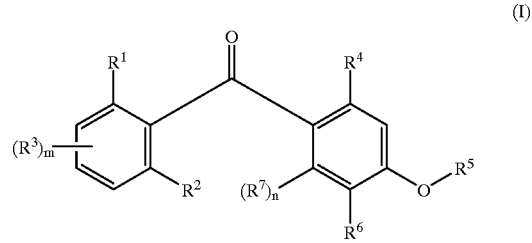

wherein $R^1$, $R^2$, $R^3$, $R^4$, $R^5$, $R^6$, $R^7$, m and n have the meaning given; and at least one compound of formula II

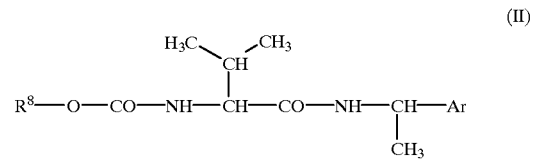

in which Ar and $R^8$ have the meaning given.

The composition is useful in a method of controlling the growth of phytopathogenic fungi at a locus. The method comprises applying synergistically effective amounts of (a) and (b) to the locus.

5 Claims, No Drawings

FUNGICIDAL MIXTURES

This application claims the benefit of provisional applications Ser. No. 60/184,277 filed Feb. 23, 2000.

DESCRIPTION

The present invention relates to a fungicidal composition comprising a fungicidally acceptable carrier and/or surface active agent and synergistically effective amounts of (a) at least one benzophenone of formula I

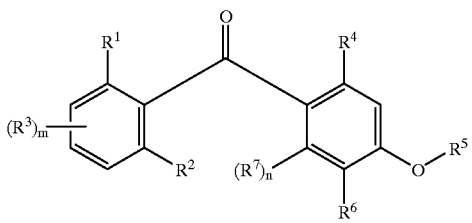

(I)

wherein
$R^1$ represents a halogen atom, an optionally substituted alkyl, alkanoyloxy, or alkoxy group; alkoxy group or a hydroxy group;
$R^2$ represents a halogen atom or an optionally substituted alkyl group,
m is 0 or an integer of 1 to 3;
$R^3$ independently represents a halogen atom, an optionally substituted alkyl or alkoxy group or a nitro group;
$R^4$ represents a halogen atom, a cyano, carboxy, hydroxy or nitro group or an optionally substituted alkyl, alkoxy, alkenyl, alkylthio, alkylsulphinyl, alkylsulphonyl or amino group;
$R^5$ represents an optionally substituted alkyl group;
$R^6$ represents a halogen atom or a nitro group, an optionally substituted alkyl, alkoxy, alkenyloxy, alkynyloxy, alkylthio, cycloalkyl, cycloalkyloxy, aryloxy group;
n is 0 or 1; and
$R^7$ independently represents a halogen atom, an optionally substituted alkyl, alkenyl, alkynyl, alkoxy, alkenyloxy, alkynyloxy, cycloalkyl, cycloalkoxy group; and (b) at least one valinamid of formula II

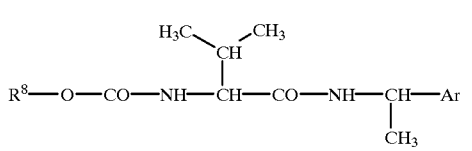

(II)

in which
$R^8$ represents alkyl and
Ar represents Aryl or hetaryl, whereby
aryl represents a phenyl or napthyl moiety, and
heteroaryl represents a benzthiazolyl, benzimidazolyl or benzoxazoyl moiety,
where if desired, these aromatic radicals can carry one to three substituents selected from the group consisting of halogen, $C_{1-6}$ alkyl and $C_{1-6}$ alkoxy.

The fungicidal compounds of formula I to be used according to the present invention are known for example from U.S. Pat. No. 5,773,663. In addition, U.S. Pat. No. 5,773,663 suggests to combine fungicidal benzophenone derivatives with other fungicides.

However, there is no hint that such mixtures show synergistic effects and can advantageously be used for controlling diseases such as grape downy mildew or others. The fungicidal compounds of formula 11 are known for example from EP 0 472 996, DE-A 43 21 897, WO-A 96 07638, DE 1 9531 814 and JP-A 09 323984.

Although mixtures comprising either benzophenones of formula I (EP 1023834) or valinamides of formula II (WO 99 56551) as active ingredients are described, mixtures comprising both benzophenones and valinamides have not been described yet.

Surprisingly, a strong synergy between the compounds of formula I and the compounds of formula II in greenhouse trials was found when these two compounds were in-tank mixed and when the activity of these mixtures was compared with that of the solo activity of each active ingredient.

A mixture of fungicides shows synergistic effect if the fungicidal activity of the mixture is larger than the sum of activities of the separately applied compounds. The expected fungicidal activity for a given mixture of two fungicides can also be calculated as follows (See Colby, S. R., "Calculating synergistic and antagonistic response of herbicide combinations", Weeds 15, pp 20–22 (1967)):

$$EE = xX + Y - X \cdot Y/100$$

wherein
x is the efficacy in % compared with an untreated control upon treatment with a fungicidal active ingredient A at a dose rate a;
y is the efficacy in % compared with an untreated control upon treatment with a fungicidal active ingredient B at a dose rate b;
EE is the expected efficacy with a combination of fungicidal active ingredients A and B at a dose of a+b, respectively.

If the actual efficacy (E) exceeds the expected (calculated) one (EE), the mixture displays a synergistic effect.

The present invention includes a fungicidal composition comprising an acceptable carrier and/or surface active agent and synergistically effective amounts of at least one compound of formula I, and at least one compound of formula II.

The present invention also includes a method of controlling the growth of phytopathogenic fungi at a locus which comprises applying synergistically effective amounts of at least one benzophenone of formula I and at least one compound of formula II as defined above to the locus.

All moieties mentioned for the substituents $R_1$ to $R_7$ of formula I as well as $R_8$ and the substituents of the Aryl moiety of formula II, $R^9$ and $R^{10}$ are collective terms for individual enumerations of the individual members of a group. For all alkyl moieties and the alkyl moieties of alkoxy, alkanoyloxy, alkylthio, alkylsulfonyl and alkylsulfinyl a $C_{1-6}$ alkyl moiety is preferred. For all alkenyl moieties or the alkenyl moieties of alkenyloxy a $C_{2-6}$ alkenyl moiety is preferred. For all alkynyl moieties or the alkynyl moieties of alkynyloxy a $C_{2-6}$ alkynyl moiety is preferred. For all cycloalkyl moieties or the cycloalkyl moieties of cycloalkyloxy a $C_{3-8}$ alkyl moiety is preferred.

For example
halogen is fluorine, chlorine, bromine and iodine;
alkyl is straight-chain or branched alkyl groups having 1 to 6 carbonatoms such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$C_{3-6}$ cycloalkyl or the cycloalkyl moiety of cycloalkoxy is a monocyclic alkyl groups having 3 to 6 carbon ring members, eg. cyclopropyl, cyclobutyl, cyclopentyl and cyclohexyl;

$C_{2-6}$ alkenyl is a straight-chain or branched alkenyl groups having 2 to 6 carbon atoms and a double bond in any desired position, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl- 2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1 -butenyl, 3,3-dimethyl-2-butenyl, 1-ethyl-1-butenyl, 1 -ethyl-2-butenyl, 1 -ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_{2-6}$ alkynyl is a straight-chain or branched alkynyl groups having 2 to 6 carbon atoms and a triple bond in any desired position, such as ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

aryl or aryloxy is an aromatic mono- or polycyclic hydrocarbon radical which is bonded to the structure directly or (aryloxy) via an oxygen atom (—O—) e.g., phenyl and naphthyl, or phenoxy and naphthyloxy;

Hetaryl is a benzo-fused 5-membered heteroaryl, containing one to two nitrogen atom and/or an oxygen or sulfur atom, e.g. bezhiazolyl, benzimidazolyl or bezoxazolyl;

Halophenyl is a phenyl moiety, substituted with 1 to 5 halogen atoms in position 2, 3, 4, 5 and/or 6;

Fluorophenyl is a phenyl moiety, substituted with 1 to 5 fluorine atoms in position 2, 3, 4, 5 and/or 6;

Alkylphenyl is a phenyl moiety, substituted with 1 to 5 $C_{1-6}$ alkyl moieties in position 2, 3, 4, 5, and/or 6;

Methylphenyl is a phenyl moiety substituted with 1–5 methyl moieties in position 2, 3, 4, 5 and/or 6;

Preferred compounds of formula I are benzophenones of formula IA,

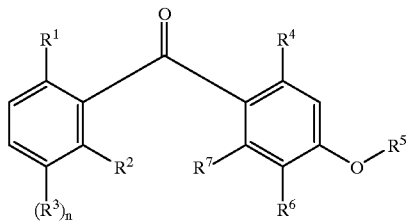

(IA)

wherein $R^1$ represents a halogen atom, a methyl, trifluoromethyl, a $C_{1-4}$ alkoxy group or hydroxy group, in particular a chlorine atom, a methyl, an acetoxy or methoxy group or hydroxy group;

$R^2$ represents a halogen atom, in particular a chloro atom or a methyl group;

$R^3$ represents a bromo or chloro atom, a methyl, trifluoromethyl or nitro group, in particular a bromine or chlorine atom, or a methyl group;

$R^4$ represents a methyl group;

$R^5$ represents an alkyl group, most preferred in a $C_{1-4}$ alkyl group, in particular a methyl group;

$R^6$ and $R^7$ each independently represent an alkoxy group which may be substituted by a phenyl, alkylphenyl or halophenyl group, preferably $C_{1-6}$ alkoxy being optionally substituted by a phenyl, methylphenyl or fluorophenyl group, in particular methoxy, benzyloxy and 2-fluorobenzyloxy; and n is 0 or 1.

Particularly preferred are the benzophenones selected from the group consisting of 6'-butoxy-2,6-dichloro-4',5'-dimethoxy-2'-methylbenzophenone coded BP-1,2,6-dichloro-4',5'-dimethoxy-6'-(2-fluorobenzyloxy)-2'-methylbenzophenone coded BP-2,6'-benzyloxy-4',5'-dimethoxy-2,6-dimethyl-2'-methylbenzophenone coded BP-3, 5-bromo-2',6-dimethyl-2,4',5',6'-tetramethoxybenzophenone coded BP-4 and 2,6-dichloro-2'-methyl-4',5',6'-trimethoxybenzophenone coded BP-5, most preferred is BP-4.

In valinamides of formula II, $R^8$ represents a $C_{1-6}$ alkylgroorup, particularly preferred a branched $C_{1-6}$ alkyl group most preferred an isopropyl or sec-butyl group.

Preferred compounds of formula II are valinamides of formula II A

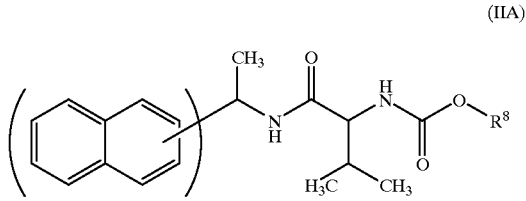

wherein
aryl represents naphthyl, most preferred bonded to the structure via position 2
wherein most preferred is compound VA1 ([2-methyl-1-[1-(naphth-2-yl)-ethylaminocarbonyl]-propyl]-carbamic acid isopropyl ester);
of formula II B

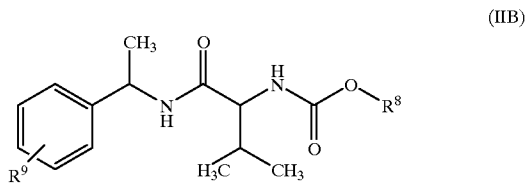

wherein
aryl represents phenyl and
$R^9$ represents halogen, most preferred chlorine, a straight, chained $C_{1-6}$ alkyl or $C^{1-6}$ alkocy group, in particular a methyl, ethyl or methoxy group, most preferred bonded to the structure via position 4,
wherein most preferred is iprovalicarb ([2-methyl-1-[1-(4-methylphenyl)-ethylaminocarbonyl]-propyl]-carbamic acid isopropyl ester);
and of formula II C

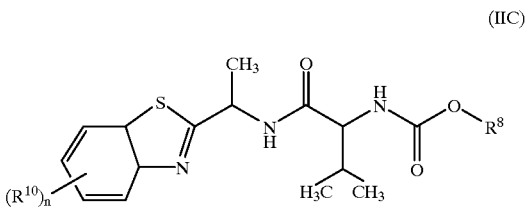

wherein
aryl represents benzthiazol-2-yl,
$R^{10}$ represents a halogen atom particularly a fluorine atom most preferred bonded to the structure in position 6 and
n has a value of 0 or 1,2 or 3, most preferred 1,
wherein most preferred is VA2, ([2-methyl-1-[1-(6-fluorobenzthiazol-2-yl)-ethylaminocarbonyl]-propyl]-carbamic acid isopropyl ester);
Preferred are co-formulations, comprising the following constituents:
a carrier;
at least one benzophenone of formula I,
at least one compound of formula II
optionally an adjuvant selected from the group consisting of polyalkoxylated alcohols, triglycerides and amines, in particular Synperonic™ 91-6, which is commercially available from Uniqema, formerly ICI Surfactants;
optionally a foam breaking agent.

The compound of formula I and the compound of formula II are to be applied together, in synergistically effective amounts. These synergistic mixtures exhibit an extraordinary efficacy against a broad range of phytopathogenic fungi, in particular against fungi from the classes ascomycetes, basidiomycetes, oomycetes and deuteromycetes. Therefore, they can be applied advantageously against a broad range of diseases in different crops. They may be applied as leaf, stem, root, into-water, seed dressing, nursery box or soil fungicides.

The mixture according to the invention may be preferably applied for controlling phytopathogenic fungi of the genera:
Achlya, Alternaria, Balansia, Bipolaris, Blumeria, Botrytis, Cercospora, Cochliobolus, Curvularia, Cylindrocladium, Drechslera, Entyloma, Erysiphe, Fusarium, Gaeumannomyces, Gerlachia, Gibberella, Guignardia, Leptosphaeria, Magnaporthe, Monilinia, Mucor, Mycosphaerella, Myrothecium, Nigrospora, Peronospora, Phoma, Phytophthora, Podosphaera, Plasmopara, Pseudoperonospora, Pseudocercosporella, Puccinia, Pyrenophora, Pyricularia, Pythium, Rhizoctonia, Rhizopus, Rhynchosporium, Sarocladium, Sclerophthora, Sclerotinia, Sclerotium, Septoria, Tilletia, Uncinula, Ustilago, Ustilaginoidea, and Venturia, in particular the species *Plasmopara viticola*, Phytophthora sp., Pseudoperonospora sp., and Bremia sp.

The mixtures according to the invention are in particular applied for controlling the above phytopathogenic fungi on dicotylydoneous plants, such as grapes, tobacco, potato, tomato, fruit crops, oil seed crops, vegetables and ornamentals, and monocotylydoneous crops.

The application rate of the compound of formula I according to this invention is usually in the range of 1 to 2000 grams of active ingredient (g a.i.) per hectare, with rates between 20–500 g g a.i./ha often achieving satisfactory control. The optimal rate for a specific application will depend on the crop(s) under cultivation and the predominant species of infesting fungi, and readily may be determined by established biological tests known to those skilled in the art.

In general, the preferred application rate of the compounds of formula I is in the range of 10 to 500 g a.i./ha, preferably 20–400 g a.i./ha.

The optimal rate for the compound of formula II will, however, depend on the crop(s) under cultivation and the level of infestation by the fungus, and can readily be determined by established biological tests.

The ratio (by weight) of the compound of formula I to the compound of formula II is as a rule, from 100:1 to 1:100. The preferred ratio formula I: formula II may vary, e.g., from about 10:1 to about 1:10, in particular from about 5:1 to about 1:5, most preferred from 3:1 to 1:3.

The active compounds can be co-formulated together in a suitable ratio according to the present invention, together with usual carriers or diluents and/or additives known in the art.

Accordingly the invention further provides a fungicidal composition which comprises a carrier and, as active ingredient, at least one compound of formula I as defined above and at least one compound of formula II as defined above.

A method of making such a composition is also provided which comprises bringing the compound of formula I and the compound of formula II into association with at least one carrier. It is also envisaged that different isomers or mixtures of isomers of formula I and/or the compound of formula II may have different levels or spectra of activity and thus compositions may comprise individual isomers or mixtures of isomers.

A composition according to the invention preferably contains from 0.1% to 99.9%, preferably 0.2 to 80% by weight (w/w) of active ingredients.

A carrier in a composition according to the invention is any material with which the active ingredient is formulated to facilitate application to the locus to be treated, which may for example be a plant, seed, foliage, soil, or into the water where the plant grow, or to the roots or to facilitate storage, transport or handling. A carrier may be a solid or a liquid, including material which is normally a gas but which has been compressed to form a liquid.

The compositions may be manufactured into e.g. emulsion concentrates, solutions, oil in water emulsions, wettable powders, soluble powders, suspension concentrates, dusts, granules, water dispersible granules, tablets, micro-capsules, gels and other formulation types by well-established procedures. These procedures include intensive mixing and/or milling of the active ingredients with other substances, such as fillers, solvents, solid carriers, surface active compounds (surfactants), and optionally solid and/or liquid auxilaries and/or adjuvants. The form of application such as spraying, atomizing, dispersing or pouring may be chosen like the compositions according to the desired objectives and the given circumstances.

Solvents may be aromatic hydrocarbons, e.g. Solvesso·200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher N-alkylpyrrolidones, e.g. N-octylpyrrolidone or N-cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite or others. The physical properties may be improved by addition of highly dispersed silica gel or polymers. Carriers for granules may be porous material, e.g. pumice, kaolin, sepiolite, bentonite; non-sorptive carriers may be calcite or sand or others. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also mean mixtures of individual surfactants.

The compositions of the invention may for example be formulated as wettable powders, water dispersible granules, dusts, granules, solutions, emulsifiable concentrates, emulsions, suspension concentrates and aerosols. Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the formulation or the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations which can be used according to the invention are:

SC-I 1

| Active ingredient | BP-1 | 100.0 g |
|---|---|---|
| Dispersing agent | Morwet D425[1] | 25.0 g |
| Dispersing agent | Pluronic ™ PE10500[2] | 5.0 g |
| Antifoaming agent | Rhodorsil ™ 426R[3] | 1.5 g |
| Dispersing agent | Rhodopol ™ 23[43] | 2.0 g |
| Antifreezing agent | Propylene glycol[4] | 80.0 g |
| Biocidal agent | Proxel ™ GXL[5] | 1.0 g |
| Water | | to 1000 ml |

SC-I 2

| Active ingredient | BP-4 | 100.0 g |
|---|---|---|
| Dispersing agent | Soprophor ™ FL[6] | 30.0 g |
| Antifoaming agent | Rhodorsil ™ 426R[3] | 1.5 g |
| Dispersing agent | Rhodopol ™ 23[4] | 2.0 g |
| Antifreezing agent | Propylene glycol | 80.0 g |
| Biocidal agent | Proxel ™ GXL[5] | 1.0 g |
| Water | | to 1000 ml |

SC-IP

| Active ingredient | iprovalicarb | 200.0 g |
|---|---|---|
| Dispersing agent | Soprophor ™ FL[6] | 25.0 g |
| Antifoaming agent | Rhodorsil ™ 426R[3] | 1.5 g |

| -continued | | |
|---|---|---|
| Dispersing agent | Rhodopol ™ 23[4)] | 2.0 g |
| Antifreezing agent | Propylene glycol | 80.0 g |
| Biocidal agent | Proxel ™ GXL[5)] | 1.0 g |
| Water | | to 1000 ml |
| SC-I + IP | | |
| Active ingredient | BP-4 | 60.0 g |
| Active ingredient | iprovalicarb | 120.0 g |
| Dispersing agent | Soprophor ™ FL[6)] | 25.0 g |
| Antifoaming agent | Rhodorsil ™ 426R[3)] | 1.5 g |
| Dispersing agent | Rhodopol ™ 23[4)] | 2.0 g |
| Antifreezing agent | Propylene glycol | 80.0 g |
| Biocidal agent | Proxel ™ GXL[5)] | 1.0 g |
| Water | | to 1000 ml |
| DC-I 1 | | |
| Active ingredient | BP-4 | 100.0 g |
| Wetting agent | Pluronic ™ PE6400[7)] | 50.0 g |
| Dispersing agent | Lutensol ™ TO 12[8)] | 50.0 g |
| Solvent | benzyl alcohol | to 1000 ml |

[1)]Morwet ™D425 (Na-salt of a naphthalene-formaldehyde-condensate; Witco)
[2)]Pluronic ™PE10500 (Polyethyleneoxid/Polypropyleneoxid block copolymer; BASF)
[3)]Rhodorsil ™426R (silicone oil; Rhône-Poulenc)
[4)]Rhodopol ™23 (Polysaccharide based dispersing agent; Rhône-Poulenc)
[5)]Proxel ™GXL (20% aqueous dipropylene glycol solution of 1,2-Benzisothiazolin-3-one; Zeneca)
[6)]Soprophor ™FL (Triethanolamoniumsalt of oxethylated polyarylphenolphosphate; Rhône-Poulenc)
[7)]Pluronic ™PE6400 (Polyethyleneoxid/Polypropyleneoxid blockcopolymer; BASF)
[8)]Lutensol ™TO12 (alkoxylated oxo-fatty acids; BASF)

The formulation SC-IP comprising a compound of formula II is in-tank mixed with any of the other formulations SC-I 1, SC-I 2, SC-I 3, or DC-I which comprise the compound of formula I.

In a preferred embodiment the active ingredients are added to the tank mix together each as solo formulation.

Therefore, the present invention relates to a kit for the preparation of a spray mixture consisting of two separate containments:
(i) a containment which comprises at least one benzophenone of formula I, in particular one or more compounds selected from BP-1 through BP-4, conventional carriers and optionally adjuvants;
(ii) a containment which comprises at least one compound of formula II.

In a preferred embodiment the said kit will consist of two bottles with dispensing means which allow the easy and correct addition of the active ingredients (a) and (b) to the tank mix.

The formulation SC-I+IP comprising BP-4 and iprovalicarb can be used directly for preparing the tank mix according to the present invention.

A composition according to the invention preferably contains from 0.5% to 95% by weight of active ingredients.

As commodity the compositions may preferably be in a concentrated form whereas the end-user generally employs diluted compositions. The compositions may be diluted down to a concentration of 0.0001% of active ingredients.

The compositions of this invention can be applied to the plants or their environment simultaneous with or in succession with other active substances. These other active substances can be either fertilizers, agents which donate trace elements or other preparations which influence plant growth. However, they can also be other fungicides, selective herbicides, insecticides, bactericides, nematicides, algicides, molluscidides, rodenticides, virucides, compounds inducing resistance into plants, biological control agents such as viruses, bacteria, nematodes, fungi and other microorganisms, repellents of birds and animals, and plant growth regulators, or mixtures of several of these preparations, if appropriate together with other carrier substances conventionally used in the art of formulation, surfactants or other additives which promote application.

Examples of insecticidal compounds are alpha-cypermethrin, benfuracarb, fenobucarb (BPMC), buprofezine, carbosulfan, cartap, chlorfenvinphos, chlorpyrifos-methyl, cycloprothrin, cypermethrin, esfenvalerate, ethofenprox, fenpropathrin, flucythrinate, flufenoxuron, hydramethyinon, imidacloprid, isoxathion, fenitrothion (MEP), fenthion (MPP), nitenpyram, phenthoate (PAP),, permethrin, propaphos, pymetrozine, silafluofen, tebufenozide, teflubenzuron, temephos, terbufos, tetrachlorvinphos and triazamate.

Examples of biological control agents are: *Bacillus thuringiensis, Verticillium lecanii, Autographica californica* NPV, *Beauvaria bassiana, Ampelomyces quisqualis, Bacilis subtilis, Pseudomonas cholororaphis, Pseudomonas fluorescens, Steptomyces griseoviridis* and *Trichoderma harzianum.*

Examples of chemical agents that induce systemic acquired resistance in plants such are: isonicotinic acid or derivatives thereof, 2,2-dichloro-3,3-dimethylcyclopropylcarboxylic acid.

The present invention is of wide applicability in the protection of crops, trees, residential and ornamental plants against fungal attack. Preferred crops are cereals, such as wheat and barley, rice as well as vines and apples. The duration of the protection is normally dependent on the individual compound selected, and also a variety of external factors, such as climate, whose impact is normally mitigated by the use of a suitable formulation. The following examples further illustrate the present invention. It should be understood, however, that the invention is not limited solely to the particular examples given below.

EXAMPLES

General Methods

The trials are carried out under greenhouse conditions in residual or curative applications. The fungicides are applied in single treatments, or in a combination comprising a benzophenone of formula I and a compound of formula II. The compounds are applied in form of an aqueous spray mix obtained from concentrated formulation or the technical material.

Grape plants of variety "Mueller-Thurgau" are grown in the greenhouse from small stake cuttings. When about 40 cm high, the number of leaves is reduced to 4 fully expanded leaves per plant.

The compounds are dissolved in acetone with 0.5% TRITON™ X155 (an alkylaryl polyether alcohol), and sprayed in concentrations and combinations as given in tables I and II with a three nozzle overhead fungicide sprayer to near run-off. Plants are then allowed to air-dry.

Inoculation precedes treatment in the case of curative evaluations and follows treatment in case of residual evaluations.

For inoculation an aqueous spore suspension of the pathogen is applied to the plant and the plants are kept 1–2 days in a moist infection chamber before being returned to the greenhouse where they are maintained by bottom watering.

Disease on the foliage as percent leaf area with disease symptoms/signs is evaluated about 7 days after inoculation.

$$\% \text{ disease control} = 100 \frac{\% \text{ disease in treated plants}}{\% \text{ disease in untreated plants}} \times 100\%$$

Two kinds of controls are included in the tests:

Plants treated with the solvent/surfactant solution and inoculated (Solvent Blank).

Untreated plants which are inoculated (Inoculated Control).

Evaluation of the disease:

Assessments of the diseases took place at the indicated day after the application of the compounds. Percent infected leaf area infected was evaluated. The efficacy of the compounds/compounds mixtures to control the diseases was calculated by using the formula given above.

Determination of synergy:

Synergy was calculated using the % disease control values of specific treatments for the two COLBY formula given hereinabove.

EXAMPLE 1

Fungicidal efficacy of the mixture of BP-4+iprovalicarb (2 day curative) against *Plasmopara viticola* on grapes The tank mix was obtained from technical materials of BP-4 and iprovalicarb. The observed and expected efficacies with different rates are given in Table I:

TABLE I

| dose rate (ppm) BP-4 | iprovalicarb | Observed Efficacy | Expected Efficacy |
|---|---|---|---|
| 27 | 0 | 2 | — |
| 9 | 0 | 0 | — |
| 3 | 0 | 0 | — |
| 1 | 0 | 0 | — |
| 0.33 | 0 | 0 | — |
| 0.11 | 0 | 0 | — |
| 0.037 | 0 | 0 | — |
| 0 | 9 | 91 | — |
| 0 | 3 | 63 | — |
| 0 | 1 | 11 | — |
| 0 | 0.33 | 2 | — |
| 0 | 0.11 | 0 | — |
| 27 | 9 | 97 | 91 |
| 9 | 9 | 96 | 91 |
| 9 | 3 | 71 | 63 |
| 3 | 3 | 73 | 63 |
| 1 | 3 | 66 | 63 |
| 3 | 1 | 15 | 11 |
| 1 | 1 | 16 | 11 |
| 0.33 | 1 | 23 | 11 |
| 1 | 0.33 | 6 | 2 |
| 0.11 | 0.33 | 5 | 2 |
| 0.33 | 0.11 | 5 | 0 |
| 0.037 | 0.11 | 3 | 0 |

EXAMPLE 2

Fungicidal efficacy of the mixture of BP-4+iprovalicarb (3 day residual) against *Plasmopara viticola* on grapes tank mix was obtained from technical materials of BP-4 and iprovalicarb. The Observed and expected efficacies with different rates are given in Table II:

TABLE II

| dose rate (ppm) BP-4 | iprovalicarb | Observed Efficacy | Expected Efficacy |
|---|---|---|---|
| 27 | 0 | 6 | — |
| 9 | 0 | 4 | — |
| 3 | 0 | 1 | — |

TABLE II-continued

| dose rate (ppm) BP-4 | iprovalicarb | Observed Efficacy | Expected Efficacy |
|---|---|---|---|
| 1 | 0 | 0 | — |
| 0.33 | 0 | 0 | — |
| 0.11 | 0 | 0 | — |
| 0.037 | 0 | 0 | — |
| 0 | 9 | 90 | — |
| 0 | 3 | 55 | — |
| 0 | 1 | 11 | — |
| 0 | 0.33 | 3 | — |
| 0 | 0.11 | 0 | — |
| 9 | 9 | 95 | 90 |
| 9 | 3 | 68 | 57 |
| 3 | 3 | 69 | 55 |
| 1 | 3 | 63 | 55 |
| 3 | 1 | 26 | 12 |
| 1 | 1 | 33 | 11 |
| 0.33 | 1 | 20 | 11 |
| 1 | 0.33 | 5 | 3 |
| 0.11 | 0.33 | 8 | 3 |
| 0.33 | 0.11 | 5 | 0 |
| 0.037 | 0.11 | 6 | 0 |

What is claimed is:

1. A fungicidal composition comprising a fungicidally acceptable carrier and/or surface active agent together with synergistically effective amounts of (a) a benzophenone of the formula

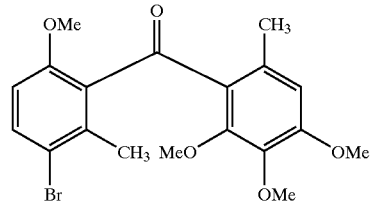

and (b) a valinamid of the formula

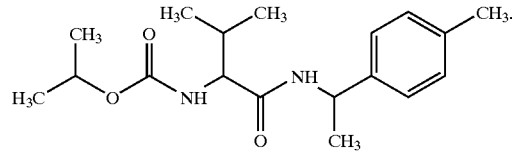

2. A composition as claimed in claim 1, wherein the ratio (by weight) of the benzophenone to the valinamid compound of formula His from 10:1 to 1:10.

3. A composition as claimed in claim 2, wherein the ratio (by weight) of the benzophenone to the valinamid is from 5:1 to 1:5.

4. A method of controlling the growth of fungi at a locus which comprises applying a composition as claimed in claim 1, to the locus.

5. A method of controlling the growth of downy mildew at a locus which comprises applying a composition as claimed in claim 1, to the locus.

* * * * *

UNITED STATES PATENT AND TRADEMARK OFFICE
CERTIFICATE OF CORRECTION

PATENT NO. : 6,696,497 B2
DATED : February 24, 2004
INVENTOR(S) : Ewald Sieverding It is certified that error appears in the above-identified patent and that said Letters Patent is hereby corrected as shown below:

Column 12,
Lines 53-54, delete "com- pound of formula H".

Signed and Sealed this

Twenty-seventh Day of July, 2004

JON W. DUDAS
*Acting Director of the United States Patent and Trademark Office*